United States Patent
Nippoldt et al.

(10) Patent No.: US 7,439,069 B2
(45) Date of Patent: Oct. 21, 2008

(54) BLOOD COAGULATION TEST CARTRIDGE, SYSTEM, AND METHOD

(76) Inventors: Douglas D. Nippoldt, 7601 Northland Dr., Brooklyn Park, MN (US) 55428; Cynthia T. Clague, 7601 Northland Dr., Brooklyn Park, MN (US) 55428; Daniel G. Ericson, 7601 Northland Dr., Brooklyn Park, MN (US) 55428

( * ) Notice: Subject to any disclaimer, the term of this patent is extended or adjusted under 35 U.S.C. 154(b) by 812 days.

(21) Appl. No.: 11/047,026

(22) Filed: Jan. 31, 2005
(Under 37 CFR 1.47)

(65) Prior Publication Data
US 2005/0255601 A1 Nov. 17, 2005

Related U.S. Application Data

(60) Provisional application No. 60/548,438, filed on Feb. 27, 2004.

(51) Int. Cl.
*G01N 33/86* (2006.01)
(52) U.S. Cl. .................... 436/69; 436/63; 436/148; 436/180; 422/68.1; 422/73; 422/100; 435/13; 73/64.41; 600/369
(58) Field of Classification Search ............. 436/63, 436/69, 148, 174, 180; 422/68.1, 73, 100; 435/13; 73/64.41; 600/369
See application file for complete search history.

(56) References Cited

U.S. PATENT DOCUMENTS

| | | | |
|---|---|---|---|
| 3,053,078 A | 9/1962 | Jewett | |
| 3,695,842 A | 10/1972 | Mintz | |
| 3,766,774 A | 10/1973 | Clark | |
| 4,000,972 A | 1/1977 | Braun et al. | |
| 4,074,971 A | 2/1978 | Braun et al. | |
| 4,244,919 A | 1/1981 | Chen | |

(Continued)

FOREIGN PATENT DOCUMENTS

EP 1 503 211 2/2005

(Continued)

OTHER PUBLICATIONS

U.S. Appl. No. 10/892,000 non-final office action mailed Apr. 2, 2007, 14 pgs.

(Continued)

*Primary Examiner*—Maureen M Wallenhorst
(74) *Attorney, Agent, or Firm*—Mike Jaro; Jeffrey J. Hohenshell

(57) ABSTRACT

A system and method for determining a coagulation time, e.g., thrombin time, PT, aPTT, and ACT, of a blood sample deposited in a test cartridge is disclosed. The test cartridge includes a blood receptacle that is open to the atmosphere into which a blood sample is to be deposited, a vacuum port that is open to atmosphere, and a spiral capillary within the test cartridge having a capillary length and cross-section area, a first capillary end of the spiral capillary open to the blood receptacle and a second capillary end of the spiral capillary open to the vacuum port, whereby the spiral capillary is closed to atmosphere. When a blood sample is deposited in the blood receptacle, a vacuum is drawn through the vacuum port and the blood is drawn through the spiral capillary until coagulation occurs. A pressure change is detected, and the coagulation time is measured.

62 Claims, 4 Drawing Sheets

U.S. PATENT DOCUMENTS

| | | |
|---|---|---|
| 4,533,519 A | 8/1985 | Baugh et al. |
| 4,534,939 A | 8/1985 | Smith et al. |
| 4,599,219 A | 7/1986 | Cooper et al. |
| 4,604,894 A | 8/1986 | Kratzer et al. |
| 4,659,550 A | 4/1987 | Schildknecht |
| 4,662,127 A | 5/1987 | Glode |
| 4,725,554 A | 2/1988 | Schildknecht |
| 4,752,449 A | 6/1988 | Jackson et al. |
| 4,774,057 A | 9/1988 | Uffenheimer et al. |
| 4,780,418 A | 10/1988 | Kratzer |
| 4,782,026 A | 11/1988 | Baugh et al. |
| 4,788,139 A | 11/1988 | Ryan |
| 4,849,340 A | 7/1989 | Oberhardt |
| 4,871,677 A | 10/1989 | Baugh et al. |
| 4,952,372 A | 8/1990 | Huber |
| 4,954,087 A | 9/1990 | Lauks et al. |
| 4,964,728 A | 10/1990 | Kloth et al. |
| 5,039,617 A | 8/1991 | McDonald et al. |
| 5,051,239 A | 9/1991 | von der Goltz |
| 5,089,422 A | 2/1992 | Brubaker |
| 5,104,808 A | 4/1992 | Laska et al. |
| 5,110,727 A | 5/1992 | Oberhardt |
| 5,124,661 A | 6/1992 | Zelin et al. |
| 5,171,538 A | 12/1992 | Tremmel et al. |
| 5,174,961 A | 12/1992 | Smith |
| 5,184,188 A | 2/1993 | Bull et al. |
| 5,248,616 A | 9/1993 | Beckman et al. |
| 5,266,462 A | 11/1993 | Hemker et al. |
| 5,296,379 A | 3/1994 | Gorog et al. |
| 5,300,779 A | 4/1994 | Hillman et al. |
| 5,302,348 A | 4/1994 | Cusack et al. |
| 5,314,826 A | 5/1994 | Baugh |
| 5,316,730 A | 5/1994 | Blake et al. |
| 5,325,295 A | 6/1994 | Fratantoni et al. |
| 5,339,375 A | 8/1994 | Kerns |
| 5,339,830 A | 8/1994 | Blake, III |
| 5,344,754 A | 9/1994 | Zweig |
| 5,350,676 A | 9/1994 | Oberhardt et al. |
| 5,372,946 A | 12/1994 | Cusak et al. |
| 5,399,497 A | 3/1995 | Kumar et al. |
| 5,418,141 A | 5/1995 | Zweig et al. |
| 5,418,143 A | 5/1995 | Zweig et al. |
| 5,425,921 A | 6/1995 | Coakley et al. |
| 5,432,084 A | 7/1995 | Brubaker |
| 5,441,892 A | 8/1995 | Baugh |
| 5,447,691 A | 9/1995 | Sanuki |
| 5,504,011 A | 4/1996 | Gavin et al. |
| 5,508,521 A | 4/1996 | Kraft et al. |
| 5,523,238 A | 6/1996 | Varon et al. |
| 5,526,111 A | 6/1996 | Collins et al. |
| 5,534,226 A | 7/1996 | Gavin et al. |
| 5,534,336 A | 7/1996 | Nomura et al. |
| 5,540,081 A | 7/1996 | Takeda et al. |
| 5,547,850 A | 8/1996 | Nowak et al. |
| 5,554,531 A | 9/1996 | Zweig |
| 5,558,838 A | 9/1996 | Uffenheimer |
| 5,561,069 A | 10/1996 | Brigham-Burke et al. |
| 5,580,744 A | 12/1996 | Zweig |
| 5,591,403 A | 1/1997 | Gavin et al. |
| 5,599,718 A | 2/1997 | Gorog |
| 5,601,991 A | 2/1997 | Oberhardt |
| 5,602,037 A | 2/1997 | Ostgaard et al. |
| 5,612,187 A | 3/1997 | Brubaker |
| 5,628,961 A | 5/1997 | Davis et al. |
| 5,646,046 A | 7/1997 | Fischer et al. |
| 5,665,311 A | 9/1997 | Gorog et al. |
| 5,695,720 A | 12/1997 | Wade et al. |
| 5,716,796 A | 2/1998 | Bull et al. |
| 5,731,212 A | 3/1998 | Gavin et al. |
| 5,736,404 A | 4/1998 | Yassinzadeh et al. |
| 5,755,939 A | 5/1998 | Dror et al. |
| 5,789,664 A | 8/1998 | Neel et al. |
| 5,800,781 A | 9/1998 | Gavin et al. |
| 5,807,471 A | 9/1998 | Dror et al. |
| 5,821,399 A | 10/1998 | Zelin |
| 5,837,203 A | 11/1998 | Godec et al. |
| 5,849,592 A | 12/1998 | Pollema et al. |
| 5,854,076 A | 12/1998 | Kundu et al. |
| 5,854,423 A | 12/1998 | Venegas |
| 5,864,017 A | 1/1999 | Brubaker |
| 5,865,749 A | 2/1999 | Doten et al. |
| 5,888,826 A | 3/1999 | Ostgaard et al. |
| 5,916,813 A | 6/1999 | Gorog |
| 5,922,551 A | 7/1999 | Durbin et al. |
| 5,925,319 A | 7/1999 | Baugh et al. |
| 5,925,569 A | 7/1999 | Gorog et al. |
| 5,951,951 A | 9/1999 | Lane et al. |
| 5,958,716 A | 9/1999 | Kundu |
| 5,972,712 A | 10/1999 | Baugh et al. |
| 6,004,819 A | 12/1999 | Gorog et al. |
| 6,010,911 A | 1/2000 | Baugh et al. |
| 6,016,193 A | 1/2000 | Freeman et al. |
| 6,016,712 A | 1/2000 | Warden et al. |
| 6,033,628 A | 3/2000 | Kaltenbach et al. |
| 6,040,186 A | 3/2000 | Lewis et al. |
| 6,043,871 A | 3/2000 | Solen et al. |
| 6,046,051 A | 4/2000 | Jina |
| 6,054,326 A | 4/2000 | Dubus |
| 6,060,323 A | 5/2000 | Jina |
| 6,061,128 A | 5/2000 | Zweig et al. |
| 6,066,504 A | 5/2000 | Jina |
| 6,077,233 A | 6/2000 | Blake, III |
| 6,101,449 A | 8/2000 | Givens et al. |
| 6,144,444 A | 11/2000 | Haworth et al. |
| 6,149,872 A | 11/2000 | Mack et al. |
| 6,159,741 A | 12/2000 | Kratzer et al. |
| 6,189,370 B1 | 2/2001 | Neel et al. |
| 6,190,614 B1 | 2/2001 | Fukunaga |
| 6,197,494 B1 | 3/2001 | Oberhardt |
| 6,200,532 B1 | 3/2001 | Wu et al. |
| 6,221,672 B1 | 4/2001 | Baugh et al. |
| 6,232,127 B1 | 5/2001 | Lane et al. |
| 6,245,573 B1 | 6/2001 | Spillert |
| 6,315,952 B1 | 11/2001 | Sklar et al. |
| 6,338,821 B1 | 1/2002 | Jina |
| 6,344,172 B1 | 2/2002 | Afeyan et al. |
| 6,365,107 B1 | 4/2002 | Markelov et al. |
| 6,391,568 B1 | 5/2002 | Schneider et al. |
| 6,410,337 B1 | 6/2002 | Brady et al. |
| 6,416,718 B1 | 7/2002 | Maiefski et al. |
| 6,438,498 B1 | 8/2002 | Opalsky et al. |
| 6,448,024 B1 | 9/2002 | Bruegger |
| 6,451,610 B1 | 9/2002 | Gorman et al. |
| 6,472,161 B1 | 10/2002 | Baugh |
| 6,488,897 B2 | 12/2002 | Dubrow et al. |
| 6,495,104 B1 | 12/2002 | Unno et al. |
| 6,527,744 B1 | 3/2003 | Kriesel et al. |
| 6,531,095 B2 | 3/2003 | Hammer et al. |
| 6,541,262 B1 | 4/2003 | Baugh et al. |
| 6,555,064 B2 | 4/2003 | Baugh et al. |
| 6,555,066 B2 | 4/2003 | Baugh et al. |
| 6,555,381 B2 | 4/2003 | Baugh et al. |
| 6,573,104 B2 | 6/2003 | Carr, Jr. et al. |
| 6,575,017 B1 | 6/2003 | Neel et al. |
| 6,586,259 B1 | 7/2003 | Mahan et al. |
| 6,613,573 B1 | 9/2003 | Cohen |
| 6,620,310 B1 | 9/2003 | Ohara et al. |
| 6,629,057 B2 | 9/2003 | Zweig et al. |
| 6,632,678 B2 | 10/2003 | Aiken et al. |
| 6,645,768 B1 | 11/2003 | Tejidor et al. |
| 6,676,902 B2 | 1/2004 | Baugh et al. |
| 6,680,177 B2 | 1/2004 | Mize |
| 6,692,969 B1 | 2/2004 | Berg et al. |
| 6,733,471 B1 | 5/2004 | Ericson et al. |

| | | |
|---|---|---|
| 6,750,053 B1 | 6/2004 | Widrig Opalsky et al. |
| 6,761,856 B2 | 7/2004 | Baugh et al. |
| 6,790,632 B2 | 9/2004 | Zweig |
| 6,887,429 B1 | 5/2005 | Marshall et al. |
| 7,291,310 B2 * | 11/2007 | Martin et al. .................. 422/73 |
| 2001/0021355 A1 | 9/2001 | Baugh et al. |
| 2001/0053337 A1 | 12/2001 | Doktycz et al. |
| 2002/0028517 A1 | 3/2002 | Brady et al. |
| 2002/0049557 A1 | 4/2002 | Chen |
| 2002/0081741 A1 | 6/2002 | Braun, Sr. et al. |
| 2003/0027235 A1 | 2/2003 | Kraus et al. |
| 2003/0150745 A1 | 8/2003 | Teodorczyk et al. |
| 2003/0156989 A1 | 8/2003 | Safir et al. |
| 2003/0211551 A1 | 11/2003 | Mahan et al. |
| 2004/0011672 A1 | 1/2004 | Ohara et al. |
| 2004/0019300 A1 | 1/2004 | Leonard |
| 2004/0043499 A1 | 3/2004 | Lee-Alvarez |
| 2004/0072357 A1 * | 4/2004 | Stiene et al. .................. 436/69 |
| 2004/0156045 A1 | 8/2004 | Zweig et al. |
| 2004/0166590 A1 | 8/2004 | Green |
| 2004/0224416 A1 | 11/2004 | Ghai et al. |
| 2005/0006237 A1 | 1/2005 | Larkin |
| 2005/0196748 A1 | 9/2005 | Ericson |
| 2005/0255601 A1 | 11/2005 | Nippoldt et al. |

FOREIGN PATENT DOCUMENTS

| | | |
|---|---|---|
| WO | 02/063273 | 8/2002 |
| WO | 03/087817 | 10/2003 |

OTHER PUBLICATIONS

U.S. Appl. No. 10/892,000 final office action mailed Oct. 30, 2007, 7 pgs.

U.S. Appl. No. 10/826,994 non-final office action mailed Apr. 2, 2007, 13 pgs.

U.S. Appl. No. 10/826,994 final office action mailed Nov. 2, 2007, 10 pgs.

PCT International Search Report from International Application No. PCT/US2005/011775, dated Jul. 29, 2005.

Flom-Halverson et al, Assessment of Heparin Anticoagulation: Comparison of Two Commercially Available Methods; Ann. Thorac. Surg., 1999: 67: 1012-1016.

* cited by examiner

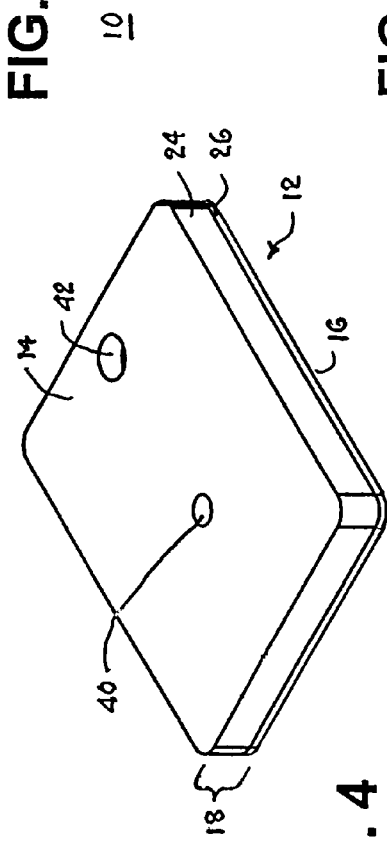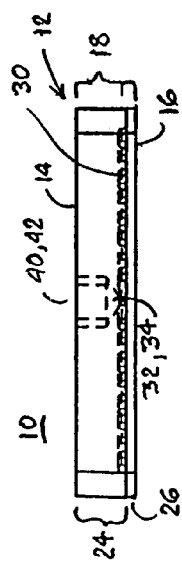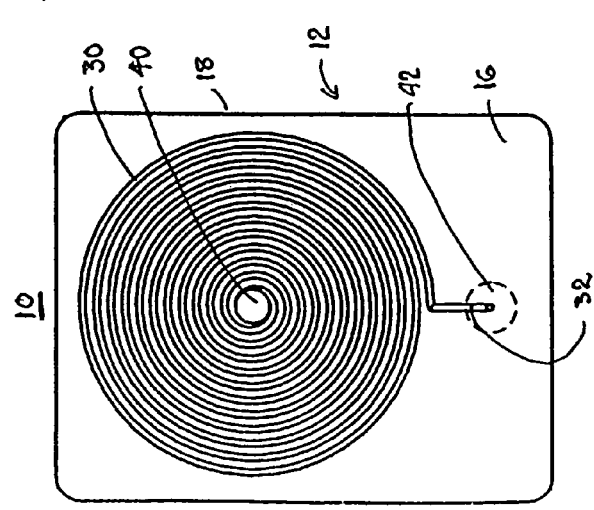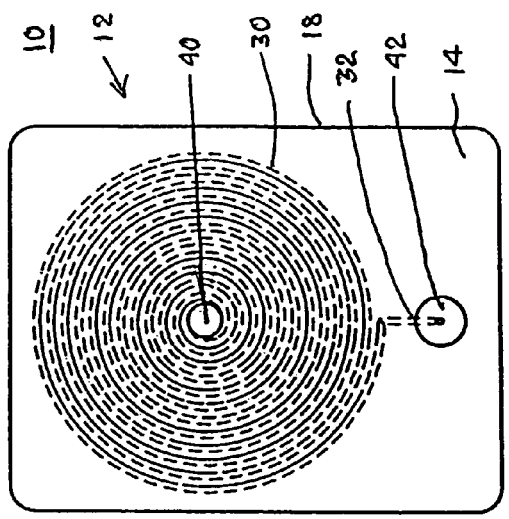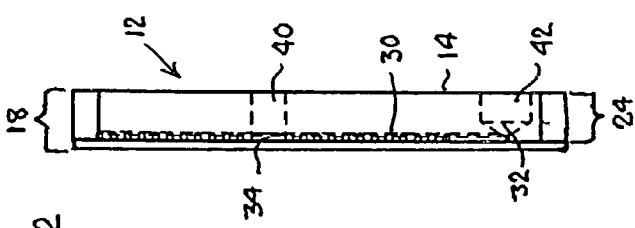

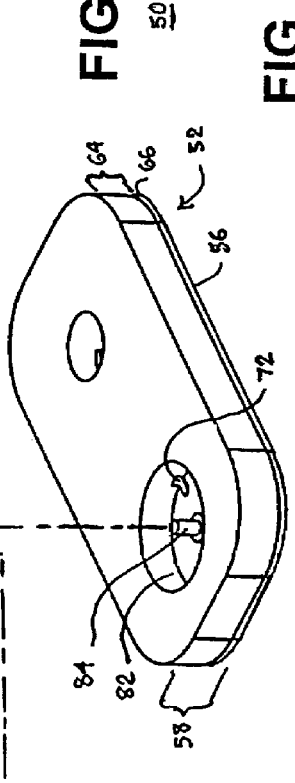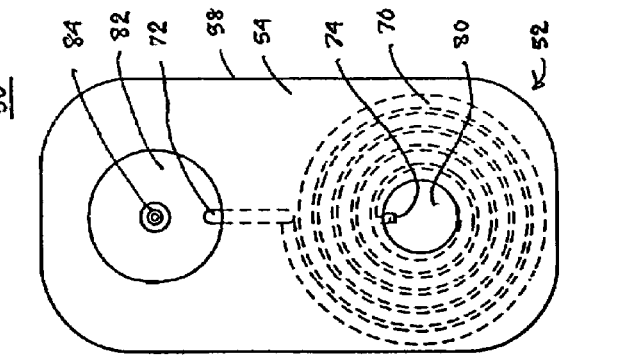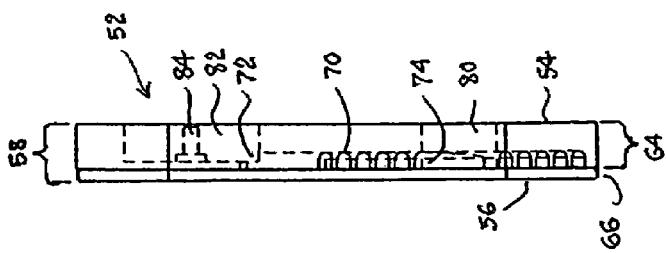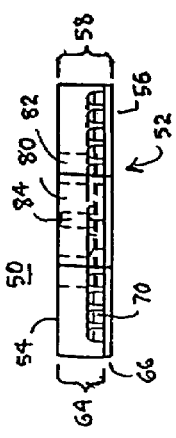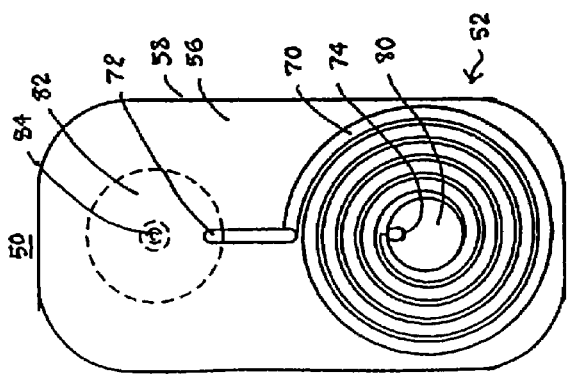

BLOOD COAGULATION TEST CARTRIDGE, SYSTEM, AND METHOD

CROSS-REFERENCE TO RELATED APPLICATION

This application claims the benefit of U.S. Provisional Application No. 60/548,438, filed Feb. 27, 2004.

FIELD OF THE INVENTION

This invention relates to measuring and detecting coagulation and coagulation-related activities in fluids, particularly human blood, and more particularly to improved methods and apparatus for obtaining a coagulation time of a blood sample.

BACKGROUND OF THE INVENTION

Blood coagulation is a complex chemical and physical reaction that occurs when blood (herein, "blood" shall mean whole blood, citrated blood, platelet concentrate or plasma, unless otherwise specified) comes into contact with an activating agent, such as an activating surface or an activating reagent. In accordance with one simplified conceptual view, the whole blood coagulation process can be generally viewed as three activities: platelet adhesion, platelet aggregation, and formation of a fibrin clot. In vivo, platelets flow through the blood vessels in an inactivated state because the blood vessel lining, the endothelium, prevents activation of platelets. When a blood vessel is damaged, however, the endothelium loses its integrity and platelets are activated by contact with tissue underlying the damaged site. Activation of the platelets causes them to become "sticky" and adhere together. Additional platelets then adhere to the activated platelets and also become activated. This process continues until a platelet "plug" is formed. This platelet plug then serves as a matrix upon which blood clotting proceeds.

If the chemical balance of the blood is suitable, thrombin is then produced that causes fibrinogen to convert to fibrin, which forms the major portion of the clot mass. During clotting, additional platelets are activated and trapped in the forming clot, contributing to clot formation. As clotting proceeds, polymerization and cross-linking of fibrin results in the permanent clot. Thus, platelet activation plays a very important function in blood coagulation.

The clinical assessment of clotting function has long been recognized to be important in the management of surgical patients. Preoperatively, the assessment of the clotting function of the patient's blood is utilized as a predictor of risk of patient bleeding, allowing advanced preparation of blood components. Perioperative monitoring of the clotting function of the patient's blood is also important because coagulopathies can be induced by hemodilution of procoagulants, fibrinogen and platelets, by consumption of coagulation factors during surgical procedures, or by cardiopulmonary bypass. Post-operative assessment of clotting function is also crucial to the patient's successful recovery. For example, 3-5% of cardiopulmonary bypass patients require surgical reoperation to stop bleeding. Prompt assessment of clotting function could rule out coagulopathy as the cause of bleeding and could avoid unnecessary surgery that adds to patient morbidity and treatment costs.

Several tests of coagulation are routinely utilized to assess the complicated cascade of events leading to blood clot formation and test for the presence of abnormalities or inhibitors of this process. Among these tests are platelet count (PLT), thrombin time, prothrombin time (PT), partial thromboplastin time (aPTT), activated clotting time (ACT), fibrinogen level (FIB) and fibrinogen degradation product concentrations. The aPTT test can also be used to assess the degree of anticoagulation resulting from heparin administration, while the PT test results can indicate the level of anticoagulation produced by warfarin administration.

During heart bypass surgery, the platelets of blood circulated in an extracorporeal circuit may become activated by contact with the materials present in the extracorporeal circuit. This activation may be reversible or irreversible. Once platelets are irreversibly activated, they lose their ability to function further. A deficiency of functional platelets in the blood may be indicative of an increased probability of a post-operative bleeding problem. Such a deficiency, and the, resulting post-operative bleeding risk, could be remedied by a transfusion of platelet concentrate. Platelet functionality tests, e.g., the ACT test, can identify a deficiency of platelets or functional platelets and aid the attending surgeon in ascertaining when to administer a platelet concentrate transfusion. Such a test is further useful in ascertaining the efficacy of a platelet transfusion. By performing the platelet functionality test following a platelet transfusion, it is possible to determine if additional platelet concentrate transfusions are indicated. Real-time assessment of clotting function at the operative site is preferred to evaluate the result of therapeutic interventions and also to test and optimize, a priori, the treatment choice and dosage.

A number of different medical apparatuses and testing methods have been developed for measuring and determining platelet activation and coagulation-related conditions of blood that can be used in real time during surgery, particularly bypass surgery, on fresh drawn blood samples or that can be used after some delay on citrated blood samples. Some of the more successful techniques of evaluating blood clotting and coagulation of fresh or citrated blood samples employ plunger techniques disclosed in commonly assigned U.S. Pat. Nos. 4,599,219, 4,752,449, 5,174,961, 5,314,826, 5,925,319, and 6,232,127, for example. These techniques are embodied in the ACT II® automatic coagulation timer, commercially sold by the assignee of this patent application.

In U.S. Pat. No. 5,302,348, an apparatus and method are disclosed for performing a coagulation time test on a sample of blood deposited in a fluid reservoir of a disposable cuvette. A capillary conduit have at least one restricted region is formed within the cuvette. The cuvette is inserted into a testing machine that engages the cuvette and draws blood from the fluid reservoir into the capillary conduit. The blood is then caused to reciprocally move back and forth within the capillary conduit so that the blood is forced to traverse the restricted region. Optical sensors of the testing machine are employed to detect movement of the blood. The testing machine measures the time required each time the blood is caused to traverse the restricted region. Coagulation is considered to have occurred and the overall coagulation time is displayed to the operator when a measured time is a predetermined percentage longer than an immediately preceding time.

In U.S. Pat. No. 5,504,011, a similar apparatus and method are disclosed for performing multiple coagulation time tests on a sample of blood deposited in a fluid reservoir of a disposable cuvette having multiple capillary conduits within the cuvette. Each of the conduits contains a dried or lyophilized activation reagent that is rehydrated by the blood. The blood in each conduit is then reciprocally moved across a restricted region of the conduit until a predetermined degree of coagulation occurs. Since the coagulation time is being monitored in multiple conduits, a representation coagulation time for a given sample can be determined. A normalizing control agent is present in at least one of the conduits. The normalizing control agent counteracts any effects of anticoagulants present in the blood sample, thereby allowing the blood sample to have generally normal coagulation characteristics. The normalized blood is tested simultaneously with the untreated blood to provide a reference value against which the functionality of the test system and the quality of the sample can be judged.

The apparatus and methods disclosed in the '348 and '011 patents only check the state of the sample during the reciprocal back and forth movement of the sample through the restricted region capillary. The detection of coagulation would be delayed or inaccurate if the sample coagulates between movement cycles.

In U.S. Pat. No. 6,200,532, a device and method for performing blood coagulation assays, particularly prothrombin times and activated partial thromboplastin times and other clotting parameters are disclosed. One embodiment of the device comprises a disposable cassette containing a sample inlet for sample delivery, a pair of interleaved spiral capillary channels for driving force, and a reaction chamber with an appropriate dry reagent for a specific assay, and a piezoelectric sensor. The device could also include a heating element for temperature control, and a magnetic bender. Compressed air is employed to drive the sample into the two spiral capillary channels. The magnetic bender is driven by an electromagnetic field generator and is attached onto a piezoelectric film in contact with the blood sample. The electric signal generated in the piezoelectric film is characterized by its frequency and amplitude due to the movement of the attached metal film. The signal collected at the site of the piezoelectric film represents the process of a biochemical reaction in the reaction chamber as the blood sample proceeds to the point at which clot formation starts and is amplified by an amplifier and rectified into a DC voltage and is sent to a recording unit and/or display unit.

Other tests can be performed on blood samples to measure coagulation that do not necessarily determine coagulation time. For example, methods and apparatus are disclosed in U.S. Pat. No. 4,780,418 for measuring the aggregation of blood platelets or the coagulation of blood drawn from a patient. The apparatus includes a capillary tube and a piston in communication with the capillary tube and connected to a motor for linear displacement thereof to draw a low pressure within the capillary tube to aspirate blood from a blood source into the capillary tube. A pressure sensor is located in the space between the drawn blood and piston, and the pressure signal is applied to a computer for comparison with a threshold. The computer calculates a motor control signal applied to the motor to regulate the pressure so that it is maintained constant in the capillary tube to mimic blood loss from a wound, for example. The computer also determines the amount of blood flowing into the capillary tube during the constant pressure regulation over a given period of time due to a known relationship relating movement of the piston to blood drawn into the cylinder. The rate of change in platelet-aggregation and blood coagulation of a patient's blood can be determined by successively employing the apparatus to draw blood samples from a patient and determine the volume drawn per unit of time.

Other blood handling equipment employ similar equipment for drawing a blood sample into a capillary tube or pipette. A system and techniques are disclosed in U.S. Pat. No. 5,540,081 for detecting clotting of a small diameter nozzle of a pipette dipped into the blood source to automatically draw a blood sample and sounding an alarm to alert an operator of the clotted pipette. The blood sample that is drawn into the pipette is apparently mixed with a reagent and tested employing other systems and techniques that are not explicitly disclosed in the '081 patent. The automatic aspiration of the required volume of blood into the pipette is complicated by partial or complete obstruction of the nozzle by incomplete or fully obstructing clots that can occur over the aspiration time. It is difficult to detect incomplete obstructing clots, and such clots can slow filling and result in incomplete filling of the pipette.

In the '081 patent, the large end of the pipette is connected to a pump through an air hose, and the pump is operated to reduce air pressure within the air hose and the pipette so that the blood sample can be aspirated into the nozzle and pipette. A pressure sensor is connected to the air hose to monitor the air pressure within the tube and develop an air pressure signal. The pressure signal is amplified by an amplifier, converted into a digital signal by an A/D converter, and applied to a plurality of pressure difference calculating circuits for comparison to a plurality of thresholds for a corresponding plurality of time periods that are selected to detect degrees of obstruction of the nozzle. An alarm circuit is included for outputting a clot detection alarm signal when at least one of said discriminating circuits discriminates that the obtained pressure difference exceeds the discrimination threshold value. The actual time that elapses between dipping the nozzle into the blood source and any clotting of the nozzle that occurs before the pipette is filled is of no importance and is not measured.

It would be desirable to provide inexpensive, relatively simple, easy to use and accurate equipment and techniques that measure one or more of the aforementioned blood coagulation times, including thrombin time, PT, aPTT, and ACT.

BRIEF SUMMARY OF THE INVENTION

Therefore, the present invention provides a compact, inexpensive, disposable, blood coagulation test cartridge into which a blood sample to be tested is deposited and a system and method for measuring one or more of the aforementioned blood coagulation times, including thrombin time, PT, aPTT, and ACT, that are simple to practice, rapid, and inexpensive.

The test cartridge comprises a blood receptacle that is open to the atmosphere into which a blood sample is to be deposited, a vacuum port that is open to atmosphere, and a spiral capillary within the cartridge having a capillary length and capillary cross-section area, a first capillary end of the spiral capillary open to the blood receptacle and a second capillary end of the spiral capillary open to the vacuum port, whereby the spiral capillary is closed to atmosphere. When a blood sample is deposited in the blood receptacle, a timer is started as a vacuum is drawn through the vacuum port, and the blood is drawn through the spiral capillary. The pressure is continuously monitored, and detection of a pressure change signifies coagulation of the blood sample in the capillary inhibiting further blood movement. The elapsed time between starting the vacuum and the pressure change constitutes a coagulation time., The blood sample may be first mixed with a reagent or coagulent before deposit in the blood receptacle, or the blood sample may be mixed with a reagent or coagulent in the blood receptacle or may contact a reagent or coagulent coating on the surfaces of the blood sample and/or the capillary spiral.

Preferred embodiments of the test cartridge are formed of a cartridge housing having a substantially box-like, i.e., prismatic, shape with first and second major sides and a minor sidewall extending between the first and second major sides and maintaining the first and second major sides in substantially parallel relation. The blood receptacle is formed in a receptacle portion of the cartridge housing between the first and second major sides and is open to atmosphere through the first major side. The vacuum port is formed in a port portion of the cartridge housing between the first and second major sides and is open to atmosphere through the first major side. The method and apparatus of the present invention employing continuously applied suction and monitoring of pressure shows the time course of the coagulation which may have advantages in minimizing false detections and providing additional information about the coagulation process.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 1 is a perspective view of one embodiment of a prismatic blood coagulation test cartridge of the present invention;

FIG. 2 is a plan view of the lower or bottom major side of the test cartridge of FIG. 1;

FIG. 3 is a plan view of the minor sidewall of the test cartridge of FIG. 1;

FIG. 4 is a plan view of the major sidewall of the test cartridge of FIG. 1;

FIG. 5 is a plan view of the upper or top major side of the test cartridge of FIG. 1;

FIG. 6 is a perspective view of a further embodiment of a prismatic blood coagulation test cartridge of the present invention having an impeller for mixing blood deposited in the cartridge blood receptacle;

FIG. 7 is a plan view of the lower or bottom major side of the test cartridge of FIG. 6;

FIG. 8 is a plan view of the minor sidewall of the test cartridge of FIG. 6;

FIG. 9 is a plan view of the major sidewall of the test cartridge of FIG. 6;

FIG. 10 is a plan view of the upper or top major side of the test cartridge of FIG. 6;

DETAILED DESCRIPTION OF THE PREFERRED EMBODIMENTS OF THE INVENTION

In the following detailed description, references are made to illustrative embodiments of methods and apparatus for carrying out the invention. It is understood that other embodiments can be utilized without departing from the scope of the invention.

Figure 11:
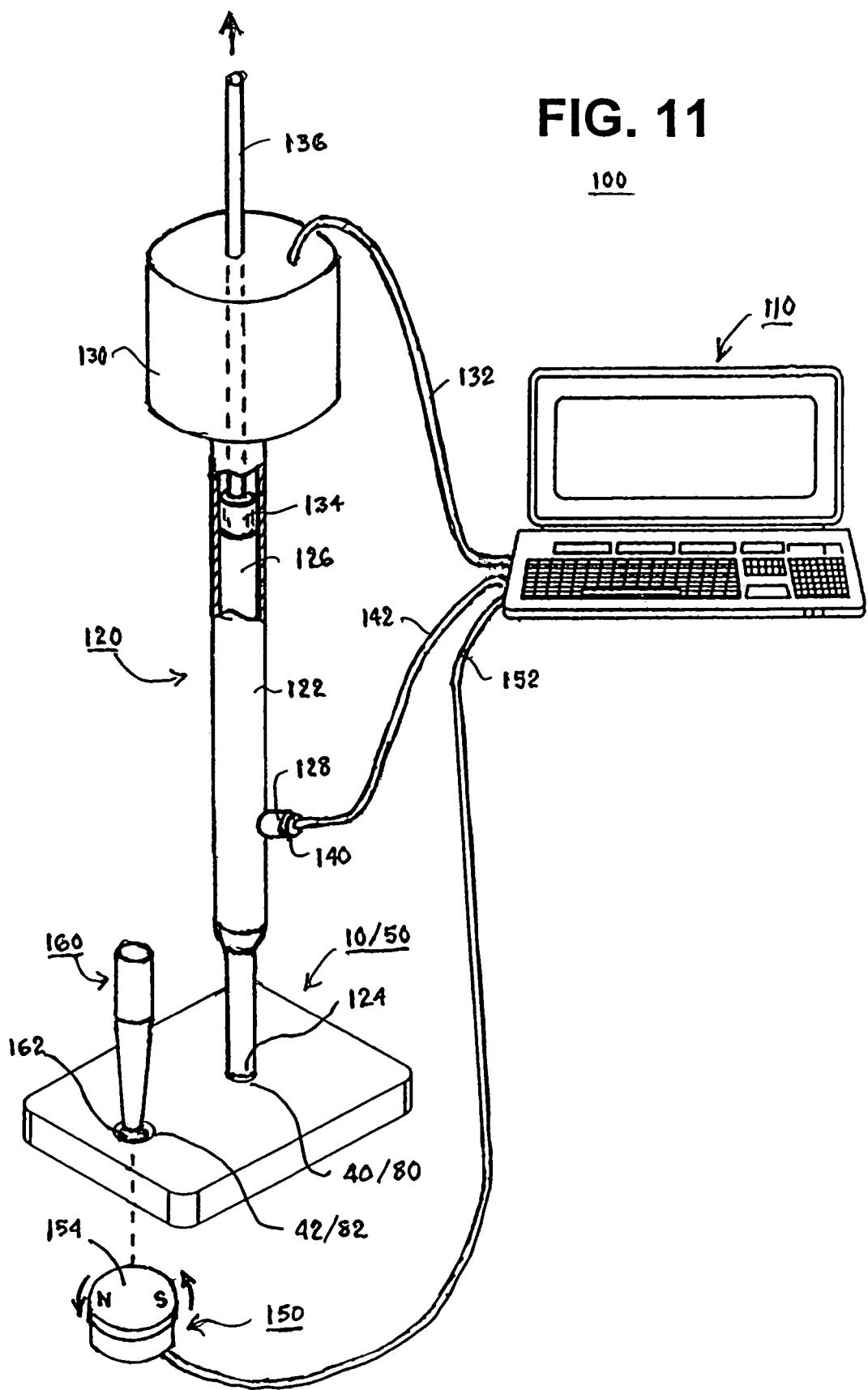
FIG. 11 is a schematic illustration of one embodiment of a system of the present invention employing the test cartridge embodiments of the present invention to determine a blood coagulation time.
Figure 12:
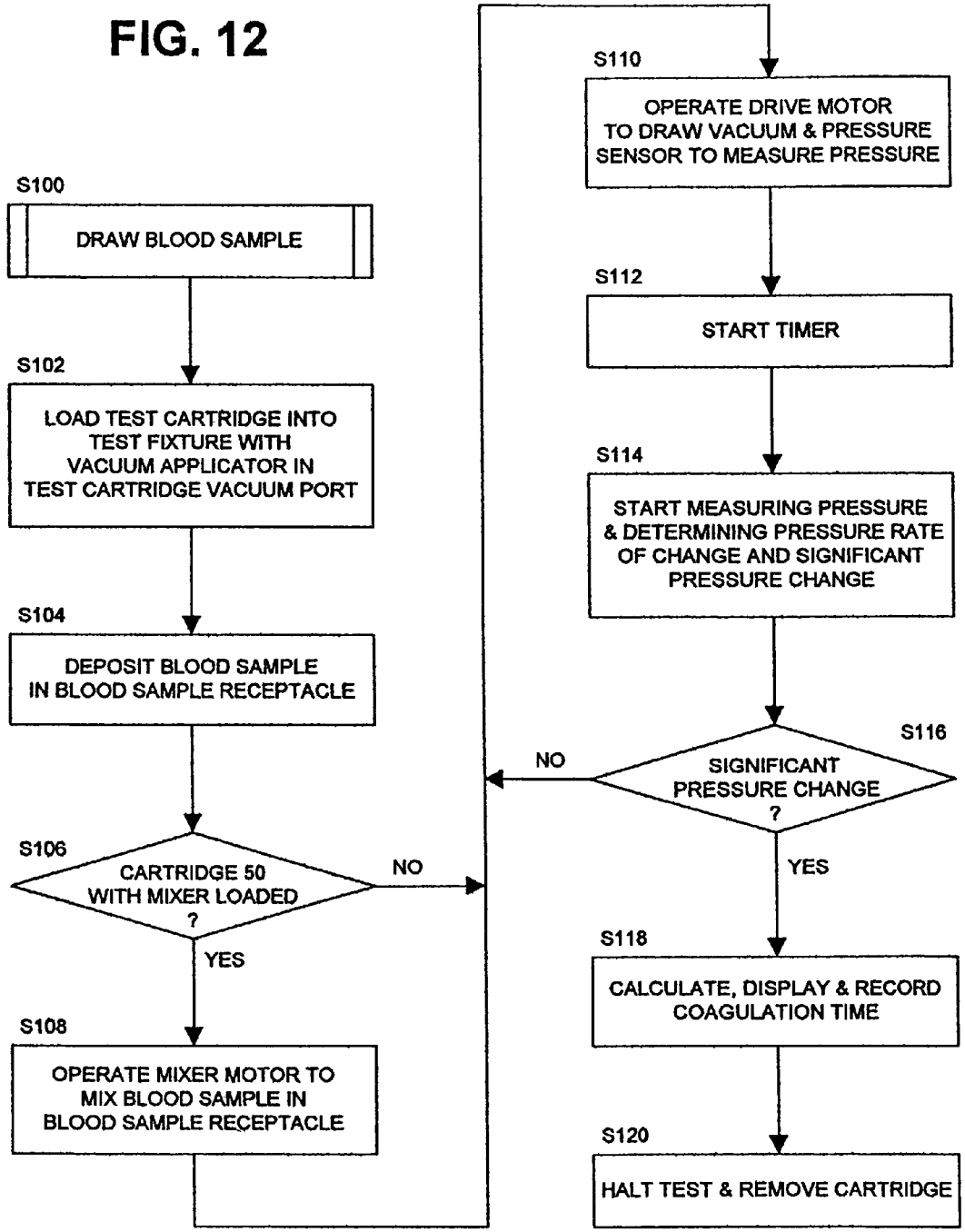
FIG. 12 is a flowchart illustrating the steps of operation of the system of FIG. 11.

A first embodiment of a test cartridge 10 used with the system 100 of the present invention depicted in FIG. 11 in accordance with the method of FIG. 12 is depicted in FIGS. 1-5. The test cartridge 10 is formed of a cartridge housing 12 having a substantially prismatic shape with first and second major sides 14 and 16 and a minor sidewall 18 extending between the first and second major sides 14, 16 and maintaining the first and second major sides 14, 16 in substantially parallel relation.

The cartridge housing 12 can be formed of a relatively thick base 24 of a transparent and relatively rigid thermoplastic material, and a relatively thin cover 26 of Mylar® plastic sheet or the like. The outer surface of the thick base 24 constitutes the first major side 14, and the outer surface of the thin cover 26 comprises the second major side 16 when the thin cover 26 is adhered against the thick base 24.

The thick base 24 is formed with a spiral capillary 30 having a capillary length and capillary cross-section area. Suitable capillary lengths are in the range of about 0.2 mm$^2$ to about 2.0 mm$^2$, and preferably about 1.0 mm$^2$. A first capillary end 32 at the outer end of the spiral capillary 30 extends into a blood well or receptacle 42, and a second capillary end 34 at the inner end of the spiral capillary 30 extends into a vacuum well or port 44. The blood receptacle 42 and the vacuum port 40 extend through the thick base 24 from the first major side 14.

The blood receptacle 42 and the vacuum port 40 can be milled through the thick base 24, and the spiral capillary 30 can be milled along one side of the thick base 24. Or, the thick base 24 can be molded in a mold shaped to form the blood receptacle 42, the vacuum port 40, and the spiral capillary 30.

The length of the spiral capillary 30 between the first and second capillary ends 32 and 34 is closed to atmosphere when the thin cover 26 is applied against and adhered to the adhesion side of the thick base 24. The adhesion may be effected by pressure or thermally activated adhesive applied to the adhesion side of the thick base 24 and/or applied in a pattern to the thin cover 26 that avoids adhesive exposed to the spiral capillary 30 or the blood receptacle 42 and vacuum port 40. In this way, the spiral capillary is formed in a capillary portion of the cartridge housing 12 between the first and second major sides 14 and 16 surrounding the vacuum port 40. The blood receptacle 42 is formed in a receptacle portion of the cartridge housing 12 between the first and second major sides 14 and 16 and is open to atmosphere through the first major side 14.

A second embodiment of a test cartridge 50 used with the system 100 of the present invention depicted in FIG. 11 in accordance with the method of FIG. 12 is depicted in FIGS. 6-10. The test cartridge 50 is also formed of a cartridge housing 52 having a substantially prismatic shape with first and second major sides 54 and 56 and a minor sidewall 58 extending between the first and second major sides 54, 56 and maintaining the first and second major sides 54, 56 in substantially parallel relation.

The cartridge housing 52 can be formed of a relatively thick base 64 of a transparent and relatively rigid thermoplastic material, and a relatively thin cover 66 of Mylar® plastic sheet or the like. The outer surface of the thick base 64 constitutes the first major side 54, and the outer surface of the thin cover 66 comprises the second major side 56 when the thin cover 66 is adhered against the thick base 64.

The thick base 64 is formed with a spiral capillary 70 having a capillary length and capillary cross-section area. Suitable capillary lengths are in the range of about 0.2 mm$^2$ to about 2.0 mm$^2$, and preferably about 1.0 mm$^2$. A first capillary end 72 at the outer end of the spiral capillary 70 extends into a blood well or receptacle 82, and a second capillary end 74 at the inner end of the spiral capillary 70 extends into a vacuum well or port 84. The blood receptacle 42 and the vacuum port 80 extend through the thick base 64 from the first major side 54.

In this embodiment, the blood receptacle 82 is modified to have a centrally disposed axle 84 extending away from the thin cover 66 toward the first major side 54. The axle 84 can be supported on a thin disk that is shaped to fit into the blood receptacle 82 that is adhered to the inner surface of the thin cover 66. Alternatively, the blood receptacle 82 can be formed in the thick base 64 having a closed end with the axle 84 extending from the closed end In addition, an impeller 90 is supported along the length of the axle 84 for rotation about the axle 84. The impeller 90 can be formed as a propeller or opposed fins or paddles or a blade with perforations as illustrated in the alternative depictions in FIG. 6. Movement of the impeller 90 causes the blood sample and reagents to be mixed together to ensure sample is evenly activated. The impeller 90 is preferably formed of a metal that is magnetizable or responds to a magnetic field. A motor driven or hand driven magnet can be applied in proximity to the second surface 56 in axial alignment with the axle 84 and rotated. The rotating magnetic field that is produced envelops the rotor 90 and causes it to rotate about the axle 84, whereby the rotating rotor 90 can mix blood deposited into the blood receptacle 82.

The blood receptacle 82 and the vacuum port 80 can be milled through the thick base 64, and the spiral capillary 70 can be milled along one side of the thick base 64. Or, the thick base 64 can be molded in a mold shaped to form the blood receptacle 82, the vacuum port 80, and the spiral capillary 70.

The length of the spiral capillary 70 between the first and second capillary ends 72 and 74 is closed to atmosphere when the thin cover 66 is applied against and adhered to the adhesion side of the thick base 64. The adhesion may be effected by pressure or thermally activated adhesive applied to the adhesion side of the thick base 64 and/or applied in a pattern to the thin cover 66 that avoids adhesive exposed to the spiral capillary 70 or the blood receptacle 82 and vacuum port 80. In this way, the spiral capillary is formed in a capillary portion of the cartridge housing 52 between the first and second major sides 54 and 56 surrounding the vacuum port 80. The blood receptacle 82 is formed in a receptacle portion of the cartridge housing 52 between the first and second major sides 54 and 56 and is open to atmosphere through the first major side 54.

In both embodiments, one of a reagent and a coagulent can be deposited in the blood receptacle 42, 82 or the surfaces along the length of the spiral capillary 30, 70 and/or the blood receptacle 42, 82 can be coated with a reagent or coagulent. The reagent or coagulant is selected to react with the blood sample to facilitate performance of a test on the blood sample determining one of thrombin time, PT, aPTT, and ACT. The reagent or coagulant is selected from the group consisting of kaolin, celite, ellagic acid, glass particles, thrombin, thromboplastin or other activating reagents. The blood receptacle may also contain reagents to counteract any anticoagulants present in the sample. During interventional procedures, heparin may be administered to mitigate coagulation induced by the procedure, in which case protamine in the blood receptacle could counteract heparin and return the sample to a baseline condition. The blood receptacle may also contain no reagent thereby providing a sample with no alteration as a reference.

The test cartridges 10, 50 can be employed in the system 100 depicted in FIG. 11 operating in accordance with the steps of the method depicted in FIG. 12. Certain of the method steps are practiced by an algorithm and/or circuitry of a preferably microcomputer-based controller 110 depicted for example as a portable personal computer.

The system 100 further comprises a vacuum applicator 120 comprising an elongated applicator body 122 extending between a vacuum or drive motor 130 and a vacuum applicator port 124 adapted to be fitted to or into the vacuum port 40, 80 to close the vacuum port from atmosphere. The applicator body 122 encloses a vacuum chamber 126 that extends from the vacuum applicator port 124 to the drive motor 130

A side port 128 extends from the applicator body 122 between the drive motor 130 and the vacuum applicator port 124 to a pressure sensor 140 that is coupled by a cable 142 to an input of the controller 110 or a module (not shown) coupled to an input of the controller 110.

A blood sample source 160, e.g., syringe or a pipette filled with a patient's blood is directed over the blood receptacle 42, 82 to deposit a blood sample 162 into the blood receptacle 42, 82.

A portion of the vacuum chamber 126 between the side port 128 and the drive motor 130 forms a vacuum cylinder that is traversed by a piston 134 coupled to a piston rod 136 extending through drive motor 130. The drive motor 130 coupled by rod 136 to the piston 134 is adapted to be operated following deposition of a blood sample in the blood receptacle 42, 82 to move the piston 134 at a predetermined fixed rate within the vacuum cylinder that creates a vacuum in the spiral capillary 30, 70 sufficient to aspirate the blood sample 162 in the blood receptacle 42, 82 along the spiral capillary 30, 70 toward the vacuum port 40, 80 until a blood clot is formed that blocks further blood aspiration.

The drive motor 130 preferably comprises a continuous or stepper motor that can be operated to move the piston 136 at a rate that is determined in controller 110 and commanded by a signal applied to the drive motor via the motor cable 132. The drive motor 130 preferably comprises a Harvard Pump II Plus syringe pump available from Harvard Apparatus Co., Holliston, Mass. Such a drive motor 130 can be operated at a rate that can draw a vacuum or push a fluid over a range of rates, dependent upon the specific coagulation test being run (certain coagulation tests take longer to complete than others). The range could be from about 0.01 ml/min to about 10 ml/min.

The pressure sensor 140 coupled to the vacuum chamber 126 is operable to measure the vacuum within the vacuum chamber 126 and develop an air pressure signal in cable 142 during movement of the piston 134. Cable 142 is coupled to an input/output of controller 110 or alternatively to a circuit module that is in turn coupled to an input/output of the controller 110. A pressure change detection circuit is preferably provided in controller 110 or the circuit module coupled between the cable 142 and an input/output of controller 110. The pressure change detection circuit can comprise an ADC for sampling and digitizing the pressure sensor signal and an algorithm to calculate the rate of change of the pressure signal. The viscosity of the sample 162 increases as the fibrin begins to form in the sample 162 thereby requiring more vacuum to pull the sample 162 through the spiral capillary 30. A significant increase in the rate of change (a deflection/inflection of the pressure signal) indicates the start of coagulation, and a clot detection signal is then generated.

The controller 110 starts a hardware or software timer when the drive motor 130 commences to move the piston 134 or when a predetermined pressure level is sensed by pressure sensor 140. In either case, the elapsed time between the imposition of the vacuum and generation of a clot detection signal is measured, thereby determining a coagulation time.

When a cartridge 50 is employed, a mixing motor 150 is also activated by a signal from controller 110 through cable 152 to rotate the magnet 154, whereby the rotating magnetic field is adapted to engage and rotate the impeller 90 to mix the blood sample 162 deposited in the blood receptacle 82 of cartridge 50.

It will be understood that mixing motor 150, axle 84, and impeller 90 may take other forms. For example, a mixing motor may be employed that directly or indirectly rotates an impeller about an axle or directly or indirectly rotates an axle fixed to a rotor. Moreover, the axle and rotor may be introduced into the blood receptacle when the blood sample 162 is deposited to effect the mixing of the blood sample 162.

Thus, the suction in vacuum chamber 126 draws blood from the deposited blood sample 162 through the spiral capillary 30, 70 to aspirate the blood in the receptacle 42, 82 along the spiral capillary 30, 70 toward the vacuum port 40, 80 until a blood clot is formed that significantly alters the vacuum pressure required to pull the fluid through the capillary.

Turning to FIG. 12, the blood sample 162 is drawn in step S100 in any conventional manner into the blood sample source 160. In step S102, one of the test cartridges 10 and 50 is loaded into the test fixture 100 with the vacuum applicator 124 inserted into the vacuum port 40, 80 as shown in FIG. 11 and deposited into the blood receptacle 42, 82. The blood sample 162 is deposited into the blood receptacle 42, 82 in step S104, either prior to or after step S102.

The controller 110 is operated to commence mixing of the blood sample 162 by the rotor 90 in step S108 if a test cartridge 50 is loaded into the test fixture 100 in step S102 as determined in step S106. It will be understood that the impeller motor 150 can be operated but will have no effect if a test cartridge 10 is loaded into the test fixture in step S102.

The controller is then operated to simultaneously commence steps S110, S112, S114, and S116. In step S110, the drive motor 130 is operated to retract the piston 134 at a programmed rate of travel and the pressure sensor signal is sampled and digitized. By maintaining a constant rate of travel of the piston, a constant rate of blood is drawn in to the spiral capillary. As long as the fluid viscosity is constant, the pressure reading is proportional to the amount of blood in the capillary, and the pressure reading changes at a slow but steady rate. As the sample starts forming a clot, the viscosity increases and the pressure reading changes sharply.

The timer is started in step S112 when the vacuum is drawn in step S110, and sampled pressure signals are processed and the rate of change is calculated. The coagulation time is calculated, displayed, and recorded in step S118 when the rate of pressure change in the vacuum chamber 126 is significant to a level signifying that a clot has formed. An audible or visual alarm may also be sounded to alert the operator. The test is then terminated in step S120, and the cartridge is removed. The test cartridge housing 12, 52 is substantially transparent to enable visual verification of aspiration of blood along the spiral capillary 30, 70 until the clot occurred.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is to be understood, that within the scope of the appended claims, the invention may be practiced otherwise than as specifically described without actually departing from the spirit and scope of the present invention. The disclosed embodiments are presented for purposes of illustration and not limitation, and the present invention is limited only by the claims that follow.

The invention claimed is:

1. A system for performing a test on a blood sample determining a coagulation time comprising:
    a test cartridge comprising a blood receptacle that is open to the atmosphere into which a blood sample is to be deposited, a vacuum port that is open to atmosphere, and a spiral capillary within the test cartridge having a capillary length and cross-section area, a first capillary end of the spiral capillary open to the blood receptacle and a second capillary end of the spiral capillary open to the vacuum port, whereby the spiral capillary is closed to atmosphere; and
    a vacuum applicator having a vacuum applicator port adapted to be fitted to the vacuum port to close the vacuum port from atmosphere and further comprising:
        a vacuum applicator housing enclosing a vacuum chamber and extending between the vacuum applicator port and a vacuum cylinder;
        a piston fitted within the vacuum cylinder;
        a drive motor coupled to the piston adapted to be powered upon deposition of the blood sample in the blood receptacle to move the piston at a predetermined fixed rate within the vacuum cylinder that creates a vacuum in the spiral capillary sufficient to aspirate the blood in the receptacle along the spiral capillary toward the vacuum port until a blood clot is formed that blocks further blood aspiration;
        a pressure sensor coupled to the vacuum chamber that is operable to measure the vacuum within the vacuum chamber and develop an air pressure signal during movement of the piston;
        a pressure change detection circuit for comparing successive pressure signals to detect a change in pressure occurring when a blood clot blocks aspiration of blood through the spiral capillary and generate a clot detection signal; and
        a timer for timing the elapsed time from the commencement of the vacuum and generation of a clot detection signal, thereby determining a coagulation time.

2. The system of claim 1, wherein the test cartridge is substantially transparent to enable visual verification of aspiration of blood along the spiral capillary.

3. The system of claim 2, wherein the test cartridge is formed of a cartridge housing having a substantially prismatic shape with first and second major sides and a minor sidewall extending between the first and second major sides and maintaining the first and second major sides in substantially parallel relation.

4. The system of claim 3, wherein the blood receptacle is formed in a receptacle portion of the cartridge housing between the first and second major sides and is open to atmosphere through the first major side.

5. The system of claim 4, wherein the vacuum port is formed in a port portion of the cartridge housing between the first and second major sides and is open to atmosphere through the first major side.

6. The system of claim 5, wherein the spiral capillary is formed in a capillary portion of the cartridge housing between the first and second major sides surrounding the vacuum port.

7. The system of claim 3, wherein:
the blood receptacle is formed in a receptacle portion of the cartridge housing between the first and second major sides and is open to atmosphere through the first major side, and a blood mixing impeller is supported in the blood receptacle; and
further comprising a mixing motor adapted to engage the impeller to mix the blood sample deposited in the blood receptacle.

8. The system of claim 7, wherein one of a reagent and a coagulent is deposited in the blood receptacle to be mixed and react with the blood sample to facilitate performance of the test.

9. The system of claim 1, wherein:
the test cartridge includes a blood mixing impeller supported in the blood receptacle; and
further comprising a mixing motor adapted to engage the impeller to mix and the blood sample deposited in the blood receptacle.

10. The system of claim 9, wherein one of a reagent and a coagulent is deposited in the blood receptacle to be mixed and react with the blood sample to facilitate performance of the test on a blood sample determining one of thrombin time, prothrombin time (PT), partial thromboplastin time (aPTT), and activated clotting time (ACT).

11. The system of claim 1, wherein one of a reagent and a coagulent is deposited in the blood receptacle to react with the blood sample to facilitate performance of a test on the blood sample determining one of thrombin time, prothrombin time (PT), partial thromboplastin time (aPTT), and activated clotting time (ACT).

12. The system of claim 11, wherein the reagent or coagulant is selected from the group consisting of kaolin, celite, ellagic acid, glass particles, thrombin, thromboplastin or other activating reagents or protamine or other deactivating reagents.

13. The system of claim 1, wherein one of a reagent and a coagulent is deposited along the spiral capillary to react with the blood sample to facilitate performance of a test on the blood sample determining one of thrombin time, prothrombin time (PT), partial thromboplastin time (aPTT), and activated clotting time (ACT).

14. The system of claim 13, wherein the reagent or coagulent is selected from the group consisting of kaolin, celite, ellagic acid, glass particles, thrombin, thromboplastin or other activating reagents or protamine or other deactivating reagents.

15. The system of claim 1, wherein the spiral capillary has a cross-section in the range of about 0.2 mm$^2$ to about 2.0 mm$^2$, and preferably about 1.0 mm.

16. The system of claim 1, wherein the spiral capillary has a length in the range of about 100 mm to about 1000 mm.

17. The system of claim 1, wherein the predetermined fixed rate of movement of the piston within the vacuum cylinder is in the range of about 0.01 ml/min to about 10 ml/min.

18. The system of claim 17, wherein the vacuum drawn in the spiral capillary is sufficient to aspirate the blood in the receptacle along the spiral capillary toward the vacuum port until a blood clot is formed that increases a rate of change of the pressure signal significantly.

19. The system of claim 18, wherein the rate of change in vacuum occurring when a blood clot forms in the spiral capillary increases significantly.

20. The system of claim 1, wherein the vacuum drawn in the spiral capillary is sufficient to aspirate the blood in the receptacle along the spiral capillary toward the vacuum port until a blood clot is formed that increases a rate of change of the pressure signal significantly.

21. A method of performing a test on a blood sample determining a coagulation time comprising:
providing a test cartridge comprising a blood receptacle that is open to the atmosphere into which a blood sample is to be deposited, a vacuum port that is open to atmosphere, and a spiral capillary within the test cartridge having a capillary length and cross-section area, a first capillary end of the spiral capillary open to the blood receptacle and a second capillary end of the spiral capillary open to the vacuum port, whereby the spiral capillary is closed to atmosphere;
depositing a blood sample in the blood receptacle;
drawing a vacuum through the vacuum port that creates a vacuum in the spiral capillary sufficient to aspirate the blood in the receptacle along the spiral capillary toward the vacuum port until a blood clot is formed that blocks further blood aspiration;
measuring the vacuum drawn within the spiral capillary as blood is aspirated along the spiral capillary;
detecting a change in the measured vacuum upon formation of a blood clot that blocks further blood aspiration; and
timing the elapsed time between the commencement of the vacuum and detection of the change, thereby determining a coagulation time.

22. The method of claim 21, wherein the test cartridge is substantially transparent to enable visual verification of aspiration of blood along the spiral capillary.

23. The method of claim 22, wherein the test cartridge is formed of a cartridge housing having a substantially prismatic shape with first and second major sides and a minor sidewall extending between the first and second major sides and maintaining the first and second major sides in substantially parallel relation.

24. The method of claim 23, wherein the blood receptacle is formed in a receptacle portion of the cartridge housing between the first and second major sides and is open to atmosphere through the first major side.

25. The method of claim 24, wherein the vacuum port is formed in a port portion of the cartridge housing between the first and second major sides and is open to atmosphere through the first major side.

26. The method of claim 25, wherein the spiral capillary is formed in a capillary portion of the cartridge housing between the first and second major sides surrounding the vacuum port.

27. The method of claim 23, wherein the blood receptacle is formed in a receptacle portion of the cartridge housing between the first and second major sides and is open to atmosphere through the first major side, and a blood mixing impeller is supported in the blood receptacle; and further comprising:
operating a mixing motor to rotate the impeller to mix the blood sample deposited in the blood receptacle.

28. The method of claim 27, wherein one of a reagent and a coagulent is deposited in the blood receptacle to be mixed and react with the blood sample to facilitate performance of the test.

29. The method of claim 21, wherein the test cartridge includes a blood mixing impeller supported in the blood receptacle, and further comprising:
operating a mixing motor to rotate the impeller to mix and the blood sample deposited in the blood receptacle.

30. The method of claim 29, wherein one of a reagent and a coagulent is deposited in the blood receptacle to be mixed and react with the blood sample to facilitate performance of the test.

31. The method of claim 21, wherein one of a reagent and a coagulent is deposited in the blood receptacle to react with the blood sample to facilitate performance of a test on the blood sample determining one of thrombin time, prothrombin time (PT), partial thromboplastin time (aPTT), activated clotting time (ACT).

32. The method of claim 31, wherein the reagent or coagulent is selected from the group consisting of kaolin, celite, ellagic acid, glass particles, thrombin, thromboplastin or other activating reagents or protamine or other deactivating reagents.

33. The method of claim 21, wherein one of a reagent and a coagulent is deposited along the spiral capillary to react with the blood sample to facilitate performance of a test on the blood sample determining one of thrombin time, prothrombin time (PT), partial thromboplastin time (aPTT), activated clotting time (ACT).

34. The method of claim 33, wherein the reagent or coagulent is selected from the group consisting of kaolin, celite, ellagic acid, glass particles, thrombin, thromboplastin or other activating reagents or protamine or other deactivating reagents.

35. The method of claim 21, wherein the spiral capillary has a cross-section in the range of about 0.2 mm$^2$ to about 2.0 mm$^2$, and preferably about 1.0 mm.

36. The method of claim 21, wherein the spiral capillary has a length in the range of about 100 mm to about 1000 mm.

37. The method of claim 21, wherein the vacuum drawn in the spiral capillary is sufficient to aspirate the blood in the receptacle along the spiral capillary toward the vacuum port until a blood clot is formed that increases a rate of change of the measured vacuum significantly.

38. The method of claim 21, wherein the vacuum drawing step comprises:
applying a vacuum applicator port of a vacuum applicator to the vacuum port of the cartridge to close the vacuum port from atmosphere, the vacuum applicator further comprising a vacuum applicator housing enclosing a vacuum chamber and extending between the vacuum applicator port and a vacuum cylinder and a piston fitted within the vacuum cylinder adapted to be moved along the vacuum cylinder by a drive motor; and
operating the drive motor coupled to the piston upon deposition of the blood sample in the blood receptacle to move the piston at a predetermined fixed rate within the vacuum cylinder that creates a vacuum in the spiral capillary sufficient to aspirate the blood in the receptacle along the spiral capillary toward the vacuum port until a blood clot is formed that blocks further blood aspiration.

39. The method of claim 38, wherein the predetermined fixed rate of movement of the piston within the vacuum cylinder is in the range of about 0.01 ml/min to about 10 ml/min.

40. The method of claim 39, wherein the vacuum drawn in the spiral capillary is sufficient to aspirate the blood in the receptacle along the spiral capillary toward the vacuum port until a blood clot is formed that increases a rate of change of the measured vacuum significantly.

41. The method of claim 38, wherein the measuring step comprises:
coupling a pressure sensor to the vacuum chamber; and
operating the pressure sensor to measure the vacuum within the vacuum chamber and develop an air pressure signal during movement of the piston.

42. The method of claim 41, wherein:
the detecting step comprises comparing successive pressure signals to detect a change in vacuum occurring when a blood clot blocks aspiration of blood through the spiral capillary and generate a clot detection signal; and
the timing step comprises timing the elapsed time between the deposition of the blood sample in the blood receptacle and generation of a clot detection signal, thereby determining one of thrombin time, PT, aPTT, and ACT.

43. The method of claim 42, wherein the vacuum drawn in the spiral capillary is sufficient to aspirate the blood in the receptacle along the spiral capillary toward the vacuum port until a blood clot is formed that increases a rate of change of the pressure signal significantly.

44. A system for of performing a test on a blood sample determining a coagulation time comprising:
a test cartridge comprising a blood receptacle that is open to the atmosphere into which a blood sample is to be deposited, a vacuum port that is open to atmosphere, and a spiral capillary within the test cartridge having a capillary length and cross-section area, a first capillary end of the spiral capillary open to the blood receptacle and a second capillary end of the spiral capillary open to the vacuum port, whereby the spiral capillary is closed to atmosphere;
means operable after deposition of a blood sample in the blood receptacle for drawing a vacuum through the vacuum port that creates a vacuum in the spiral capillary sufficient to aspirate the blood in the receptacle along the spiral capillary toward the vacuum port until a blood clot is formed that blocks further blood aspiration;
means for measuring the vacuum drawn within the spiral capillary as blood is aspirated along the spiral capillary;
means for detecting a change in the measured vacuum upon formation of a blood clot that blocks further blood aspiration; and
means for timing the elapsed time between the commencement of the vacuum and detection of the change, thereby determining a coagulation time.

45. The system of claim 44, wherein the means for drawing a vacuum comprises:
a vacuum applicator comprising a vacuum applicator housing enclosing a vacuum chamber and extending between a vacuum applicator port adapted to be coupled to the vacuum port of the cartridge to close the vacuum port from atmosphere and a vacuum cylinder and a piston fitted within the vacuum cylinder adapted to be moved along the vacuum cylinder by a drive motor; and
means for operating the drive motor coupled to the piston upon deposition of the blood sample in the blood receptacle to move the piston at a predetermined fixed rate within the vacuum cylinder that creates a vacuum in the spiral capillary sufficient to aspirate the blood in the receptacle along the spiral capillary toward the vacuum port until a blood clot is formed that blocks further blood aspiration.

46. The system of claim 45, wherein the measuring means comprises:
a pressure sensor coupled to the vacuum chamber; and
means for operating the pressure sensor to measure the vacuum within the vacuum chamber and develop an air pressure signal during movement of the piston.

47. The system of claim 46, wherein:
the detecting means compares successive pressure signals to detect a change in vacuum occurring when a blood clot blocks aspiration of blood through the spiral capillary and generate a clot detection signal; and the timing means times the elapsed time between the deposition of the blood sample in the blood receptacle and generation of a clot detection signal, thereby determining one of thrombin time, PT, aPTT, and ACT.

48. The system of claim 47, wherein the test cartridge is formed of a cartridge housing having a substantially prismatic shape with first and second major sides and a minor sidewall extending between the first and second major sides and maintaining the first and second major sides in substantially parallel relation.

49. The system of claim 48, wherein the blood receptacle is formed in a receptacle portion of the cartridge housing between the first and second major sides and is open to atmosphere through the first major side.

50. The system of claim 49, wherein the vacuum port is formed in a port portion of the cartridge housing between the first and second major sides and is open to atmosphere through the first major side.

51. The system of claim 50, wherein the spiral capillary is formed in a capillary portion of the cartridge housing between the first and second major sides surrounding the vacuum port.

52. The system of claim 45, wherein the predetermined fixed rate of movement of the piston within the vacuum cylinder is in the range of about 0.01 ml/min to about 10 ml/min.

53. The system of claim 47, wherein the vacuum drawn in the spiral capillary is sufficient to aspirate the blood in the receptacle along the spiral capillary toward the vacuum port until a blood clot is formed that increases a rate of change of the pressure signal significantly.

54. The system of claim 48, wherein:
the blood receptacle is formed in a receptacle portion of the cartridge housing between the first and second major sides and is open to atmosphere through the first major side, and a blood mixing impeller is supported in the blood receptacle; and
further comprising a mixing motor adapted to engage the impeller to mix the blood sample deposited in the blood receptacle.

55. The system of claim 54, wherein one of a reagent and a coagulent is deposited in the blood receptacle to be mixed and react with the blood sample to facilitate performance of the test.

56. The system of claim 44, wherein the test cartridge is substantially transparent to enable visual verification of aspiration of blood along the spiral capillary.

57. The system of claim 44, wherein one of a reagent and a coagulent is deposited in the blood receptacle to react with the blood sample to facilitate performance of a test on the blood sample determining one of thrombin time, prothrombin time (PT), partial thromboplastin time (aPTT), activated clotting time (ACT).

58. The system of claim 57, wherein the reagent or coagulent is selected from the group consisting of kaolin, celite, ellagic acid, glass particles, thrombin, thromboplastin or other activating reagents or protamine or other deactivating reagents.

59. The system of claim 44, wherein one of a reagent and a coagulant is deposited along the spiral capillary to react with the blood sample to facilitate performance of a test on the blood sample determining one of thrombin time, prothrombin time (PT), partial thromboplastin time (aPTT), activated clotting time (ACT).

60. The system of claim 59, wherein the reagent or coagulent is selected from the group consisting of kaolin, celite, ellagic acid, glass particles, thrombin, thromboplastin or other activating reagents or protamine or other deactivating reagents.

61. The system of claim 44, wherein the spiral capillary has a cross-section in the range of about 0.2 mm$^2$ to about 2.0 mm$^2$, and preferably about 1.0 mm$^2$.

62. The system of claim 44, wherein the spiral capillary has a length in the range of about 100 mm to about 1000 mm.

* * * * *